(12) United States Patent
Muyo et al.

(10) Patent No.: US 10,292,582 B2
(45) Date of Patent: May 21, 2019

(54) OPHTHALMOSCOPES

(71) Applicant: OPTOS PLC, Dunfermline, Fife (GB)

(72) Inventors: Gonzalo Muyo, Dunfermline (GB); Derek Swan, Dunfermline (GB)

(73) Assignee: Optos PLC, Dunfermline (GB)

( * ) Notice: Subject to any disclaimer, the term of this patent is extended or adjusted under 35 U.S.C. 154(b) by 0 days.

(21) Appl. No.: 15/509,844

(22) PCT Filed: Aug. 25, 2015

(86) PCT No.: PCT/GB2015/052450
§ 371 (c)(1),
(2) Date: Mar. 8, 2017

(87) PCT Pub. No.: WO2016/038332
PCT Pub. Date: Mar. 17, 2016

(65) Prior Publication Data
US 2017/0258322 A1   Sep. 14, 2017

(30) Foreign Application Priority Data
Sep. 9, 2014  (GB) .................................. 1415915.6

(51) Int. Cl.
A61B 3/10       (2006.01)
A61B 3/135      (2006.01)
(52) U.S. Cl.
CPC ............ *A61B 3/1025* (2013.01); *A61B 3/135* (2013.01)
(58) Field of Classification Search
CPC .............................. A61B 3/1025; A61B 3/135
USPC ........................................ 351/200, 205, 214
See application file for complete search history.

(56) References Cited

U.S. PATENT DOCUMENTS

| 2010/0014052 A1 | 1/2010 | Koschmieder et al. |
| 2012/0133888 A1* | 5/2012 | Gray ............... A61B 3/1025 351/206 |
| 2015/0216408 A1* | 8/2015 | Brown ............... A61B 3/102 351/43 |

FOREIGN PATENT DOCUMENTS

| EP | 2 767 858 | 8/2014 |
| WO | WO-2010/125394 A1 | 11/2010 |
| WO | WO-2014/053824 | 4/2014 |

OTHER PUBLICATIONS

International Search Report for PCT Application No. PCT/GB2015/052450 dated Dec. 9, 2015, 2 pages.
Search Report for Application No. GB1415915.6 dated Feb. 24, 2015, 1 page.

* cited by examiner

*Primary Examiner* — Tuyen Tra
(74) *Attorney, Agent, or Firm* — Pavan K. Agarwal; Shabbi S. Khan; Foley & Lardner LLP

(57) ABSTRACT

An ophthalmoscope (10) comprising a light source (12), a first scanner (14), a first scan transfer element (16), a second scanner (18), and a second scan transfer element (20), which provide a two-dimensional scan of incident light from an apparent point source at a pupillary point of an eye (22) onto the fundus of the eye, and which descan a two-dimensional scan of return light from the fundus of the eye to provide return light from an apparent point source at the first scanner, wherein the first scan transfer element comprises a free-form element which has a shape defined to provide aberration correction of the return light from the fundus of the eye.

19 Claims, 4 Drawing Sheets

OPHTHALMOSCOPES

This application is a U.S. National Stage of International Application No. PCT/GB2015/052450, filed on Aug. 25, 2015, designating the United States, and claiming the benefit of Great Britain Patent Application No. 1415915.6, filed Sep. 9, 2014, all of which are hereby incorporated by reference in their entireties.

The invention relates to improvements in and relating to ophthalmoscopes particularly correcting for aberration and improving confocality in ophthalmoscopes.

An ophthalmoscope generally comprises a system for directing incident light from a source onto a portion of a subject's fundus, coinciding with an object plane of the ophthalmoscope, and for collecting return light from the portion of the subject's fundus in a detection system. A number of scan elements and scan transfer elements are commonly used to direct and collect the incident and return light, and the collected return light is used to form an image of the portion of the subject's fundus. In some ophthalmoscopes, for example white light, ultra wide-field ophthalmoscopes, due to the optical characteristics of the scan elements and scan transfer elements, aberrations are present in these ophthalmoscopes. The aberrations introduced into the incident and return light by the elements vary according to the position of the light on the fundus. The aberrations can cause defocussing of the light from a collimated beam, which defocussing also varies according to the position of the light on the fundus. If a standard confocal aperture is used in the detection of the fundus return light, due to the systematic aberrations, some of the fundus return light can be lost and the signal-to-noise of the fundus return light over, for example, corneal return light can be compromised.

According to a first aspect of the invention there is provided an ophthalmoscope comprising a light source, a first scanner, a first scan transfer element, a second scanner, and a second scan transfer element,
which provide a two-dimensional scan of incident light from an apparent point source at a pupillary point of the eye onto the fundus of the eye, and
which descan a two-dimensional scan of return light from the fundus of the eye to provide return light from an apparent point source at the first scanner,
wherein the first scan transfer element comprises a free-form element which has a shape defined to provide aberration correction of the return light from the fundus of the eye.

The free-form element provides aberration correction whilst maintaining an apparent point source of incident light at the pupillary point of the eye and an apparent point source of return light at the first scanner.

The free-form element may comprise a reflective element. The free-form element may comprise a static element.

The free-form element may have a shape comprising curvature in each of first and second substantially orthogonal axes of the element. The curvature along the first axis may be defined by an ellipse. The curvature along the first axis may be defined by a parabola. The curvature along the second axis may be defined by a pre-determined mathematical function. The pre-determined mathematical function may comprise at least one polynomial function. The pre-determined mathematical function may comprise a combination of polynomial functions.

The free-form element may be substantially rectangular in shape. The first axis of the element may substantially coincide with a long axis of the rectangular shape and the second axis of the element may substantially coincide with a short axis of the rectangular shape. The first axis of the element may be at an angle to the long axis of the rectangular shape and the second axis of the element may be at an angle to the short axis of the rectangular shape.

The free-form element may have a shape defined to provide aberration correction of the return light to produce return light from any location of the fundus which, at the apparent point source at the first scanner, has a substantially uniform divergence in a direction of the light which is substantially orthogonal to a direction of travel of the light and substantially parallel to the second axis of the free-form element.

The ophthalmoscope may comprise a lens positioned after the first scanner, which is used to focus the return light to produce return light from any location of the fundus which is collimated in the direction of the light substantially orthogonal to a direction of travel of the light and substantially parallel to the second axis of the free-form element. As the shaping of the free-form element produces substantially uniform divergence of the return light from any location of the fundus, the same lens can be used to produce collimation of the return light from any location of the fundus.

The two dimensional scan of the fundus of the eye may comprise a plurality of beams of return light, each beam of return light originating from a different location of the fundus of the eye. The free-form element may have a shape defined to provide aberration correction of a plurality of beams of return light originating from different locations of the fundus to produce beams of return light which, at the apparent point source at the first scanner, have a substantially uniform divergence in a direction of the beams substantially orthogonal to a direction of travel of the beams and substantially parallel to the second axis of the free-form element.

The ophthalmoscope may comprise a lens positioned after the first scanner, which is used to focus the plurality of beams of return light originating from different locations of the fundus to produce beams of return light which are collimated in the direction of the light substantially orthogonal to a direction of travel of the light and substantially parallel to the second axis of the free-form element. As the shaping of the free-form element produces substantially uniform divergence of the return light from any location of the fundus, the same lens can be used to produce collimation of each of the beams of return light from each location of the fundus.

The free-form element may have a shape defined to provide aberration correction of the incident light on the fundus of the eye. The free-form element may have a shape defined to provide aberration correction of the incident light to produce incident light at any location of the fundus which, at the apparent point source at the pupilliary point of the eye, has a substantially uniform divergence or convergence in a direction of the light substantially orthogonal to a direction of travel of the light and substantially parallel to the second axis of the free-form element.

The two-dimensional scan of incident light on the fundus of the eye may comprise a plurality of beams of incident light, each beam of incident light being incident on a different location of the fundus of the eye. The free-form element may have a shape defined to provide aberration correction of a plurality of beams of incident light incident on different locations of the fundus to produce beams of incident light which, at the apparent point source at the pupilliary point of the eye, have a substantially uniform divergence in a direction of the beams substantially orthogonal to a direction of travel of the beams and substantially parallel to the second axis of the free-form element.

The free-form element may be positioned in the ophthalmoscope such that the first axis of the element forms a substantially vertical axis and the second axis of the element forms a substantially horizontal axis. The free-form element may be positioned in the ophthalmoscope such that the first axis of the element forms a substantially horizontal axis and the second axis of the element forms a substantially vertical axis. The free-form element may be positioned in the ophthalmoscope such that the first axis of the element is at an angle to a vertical axis of the ophthalmoscope and the second axis of the element is at a corresponding angle to a horizontal axis of the ophthalmoscope.

Aberration correction in the ophthalmoscope provides an improvement in confocal detection of the return light from the fundus of the eye. Confocal detection of return light in an ophthalmoscope is used to enhance detection of light from the fundus over detection of light returned from other structures such as the cornea of the eye and elements of the ophthalmoscope.

In an ideal ophthalmoscope where there is no aberration, each beam of incident light at an entry point of the eye is collimated in all directions of the beam orthogonal to the direction of travel of the beam. The beam of incident light is then focussed by the eye to form focussed incident light on a location of the fundus of the eye. The return light from the location of the fundus of the eye is defocussed by the eye into a beam of return light at an exit point of the eye. The beam of return light is collimated in all directions of the beam orthogonal to the direction of travel of the beam at the exit point of the eye. If a conventional pinhole aperture is positioned at a plane confocal with the fundus, a lens positioned before the aperture will focus the beam of return light from the fundus to pass through the aperture at the plane confocal with the fundus. Return light from other structures will not form a focus at the pinhole aperture, i.e. at the plane confocal with the fundus, and is therefore largely filtered out.

In ophthalmoscopes, in particular wide field ophthalmoscopes, where aberration is introduced into the incident and return light, each beam of return light is not collimated in all directions of the beam orthogonal to the direction of travel of the beam at the exit point of the eye. If a conventional pinhole aperture is positioned at a plane confocal with the fundus, a lens positioned before the aperture will not be able to focus the beam of return light from the fundus such that all of the beam passes through the aperture at the plane confocal with the fundus. Therefore a proportion of the fundus return light is lost. This can be compensated for by use of a customised aperture having a larger size, but this allows more light from other structures to pass through the aperture.

In the ophthalmoscope of the present invention, correction of aberration improves the collimation of each beam of return light. If a conventional pinhole aperture is positioned at a plane confocal with the fundus, a lens positioned before the aperture is therefore better able to focus the beam of return light from the fundus through the aperture. This leads to an improvement in confocal detection of the fundus return light, over ophthalmoscopes where there is no aberration correction. Return light from other structures, such as the cornea of the eye and elements of the ophthalmoscope, will not form a focus at a plane confocal with the fundus, i.e. at the aperture, and can be filtered out.

The ophthalmoscope may further comprise fundus return light separation apparatus comprising at least one lens and an aperture. The lens may be an aspherical lens. The aperture may be a slit aperture. The slit aperture may comprise a first, long, dimension of, for example, approximately 2 mm and a second, short, dimension of, for example, approximately 250 μm.

The lens may be positioned in the ophthalmoscope to receive return light from the fundus of the eye via the first scanner. The lens may focus the fundus return light into a line of return light at a plane confocal with the fundus of the eye. The slit aperture may be positioned in the ophthalmoscope after the lens in an optical path of the return light at the plane confocal with the fundus of the eye. The slit aperture may be positioned in the ophthalmoscope such that its first axis is substantially parallel with the line of return light and the line of return light substantially passes through the slit aperture.

Return light from other structures, such as the cornea of the eye and elements of the ophthalmoscope, will not be focussed by the lens into a line of light and will substantially not pass through the slit aperture i.e. are substantially filtered out. This leads to an improvement in confocal detection of the fundus return light.

The ophthalmoscope may further comprise a static phase mask having a shape designed to provide aberration correction of the incident light on the retina of the eye.

The ophthalmoscope may comprise a wide field ophthalmoscope. The ophthalmoscope may comprise an ultra-wide field ophthalmoscope. The ophthalmoscope may operate in a reflectance mode. The ophthalmoscope may operate in a fluorescence mode. The ophthalmoscope may be used for optical coherence tomography.

Where reference is made to the fundus of an eye, it is to be understood that this includes, but is not limited to, the retina, optic disc, macula, fovea, posterior pole, Bruch's membrane and choroid of the eye.

According to a second aspect of the invention there is provided a first scan transfer element for use in the ophthalmoscope of the first aspect of the invention.

According to a third aspect of the invention there is provided a method of defining a shape of a first scan transfer element for use in the ophthalmoscope of the first aspect of the invention, comprising (i) constructing an optical description of a system comprising the ophthalmoscope,
(ii) passing a plurality of rays through the system,
(iii) determining paths of the rays through the system,
(iv) using the paths of the rays to measure aberration of at least some of the elements of the ophthalmoscope as a function of angle, and
(v) using the aberration measurement to determine a shape of the first scan transfer element.

The method may further provide compensation for aberrations of a model eye. The method may comprise (i) constructing an optical description of a system comprising the ophthalmoscope and the model eye,
(ii) passing a plurality of rays through the system to impinge at a plurality of angles on a surface of the model eye,
(iii) determining paths of the rays through the system,
(iv) using the paths of the rays to measure aberration of at least some of the elements of the ophthalmoscope and the model eye as a function of angle, and
(v) using the aberration measurement to determine a shape of the first scan transfer element.

An embodiment of the invention will now be described by way of example only with reference to the accompanying drawings in which.

Figure 1:
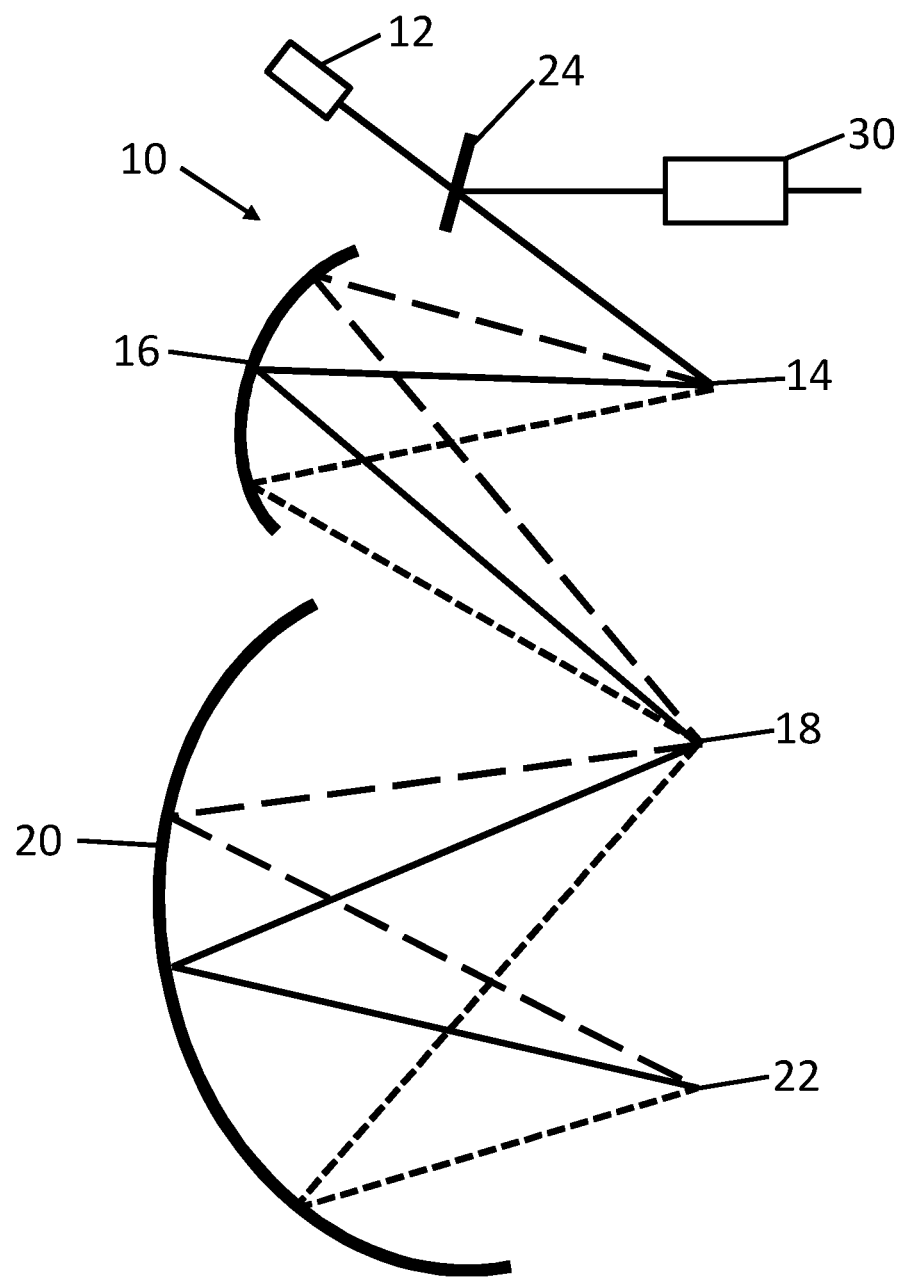
FIG. 1 is a schematic representation of an ophthalmoscope according to the first aspect of the invention.

Referring to FIG. 1 an ophthalmoscope 10 comprises a light source 12, a first scanner 14, a first scan transfer element 16, a second scanner 18, and a second scan transfer element 20. The light source 12 operates to produce a plurality of consecutive beams of incident light. The first scanner 14 is a rotating polygon and receives the incident light beams from the light source 12. In this embodiment, the first scanner 14 provides a vertical scan of the incident light beams as represented by the three beams. The first scan transfer element 16 is a free-form static, reflective element, described further below. The first scan transfer element 16 has first and second focal points, and is positioned in the ophthalmoscope 10 such that the first scanner 14 coincides with the first focal point and the second scanner 18 coincides with the second focal point, as shown. The first scan transfer element 16 thus transfers the vertical scan of the incident light beams from the first scanner 14 to the second scanner 18. The second scanner 18 is a flat mirror driven by a stepper motor and, in this embodiment, provides a horizontal scan of the incident light beams. The second scan transfer element 20 is an aspherical mirror and has first and second focal points. It is positioned in the ophthalmoscope 10 such that the second scanner 18 coincides with the first focal point and a pupillary point of an eye 22 of a subject coincides with the second focal point, as shown. The second scan transfer element 20 thus transfers the horizontal scan of the incident light beams from the second scanner 18 through the pupillary point and on to the fundus of the eye 22.

The first scanner 14, the first scan transfer element 16, the second scanner 18, and the second scan transfer element 20 therefore operate in combination to provide a two-dimensional scan of incident light beams at the fundus of the eye 22. The two-dimensional incident light scan appears to originate from an apparent point source at the pupillary point of the eye 22 and comprises a plurality of beams of incident light, each beam of incident light being incident on a different location of the fundus of the eye 22.

Return light from the fundus of the eye 22, in both reflectance and fluorescence operation modes of the ophthalmoscope 10, forms a two-dimensional scan of return light from the fundus of the eye 22. The two-dimensional scan of return light comprises a plurality of beams of return light, each beam of return light originating from a different location of the fundus of the eye. The two-dimensional scan of return light passes back through the pupilliary point of the eye 22, the second scan transfer element 20, the second scanner 18, the first scan transfer element 16 and the first scanner 14. These act to descan the two-dimensional scan of the return light to provide the plurality of beams of return light from the first scanner 14. The plurality of beams of return light appears to originate from an apparent point source at the first scanner 14. The first scanner 14 projects each of the return light beams in a direction in which the plurality of beams of incident light are received from the light source 12. The beams of return light are separated from the incident light path by a beam splitter 24 and coupled to detectors (not shown). A time series of measurements from the detectors is used to form the two-dimensional scan of the return light and produce an image of the fundus of the eye 22.

Figure 2:
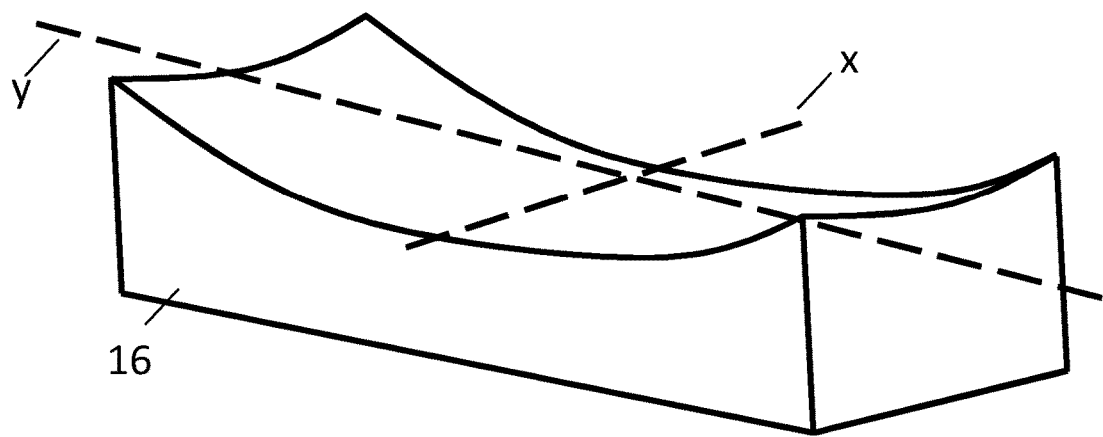
FIG. 2 is a schematic representation of a first scan transfer element according to the second aspect of the invention used in the ophthalmoscope of FIG. 1.

Referring to FIGS. 1 and 2, the first scan transfer element 16 comprises a free-form element which has a shape defined to provide aberration correction of the return light from the fundus of the eye. The free-form element 16 has a shape comprising curvature in each of first and second substantially orthogonal axes, x, y, of the element. The curvature along the first, y, axis is defined by an ellipse and the curvature along the second, x, axis is defined by a predetermined mathematical function, comprising one or more polynomial functions. The free-form element 16 is substantially rectangular in shape and the first axis, y, of the element lies at an angle to a long axis of the rectangular shape as shown and the second axis, x, of the element lies at an angle to a short axis of the rectangular shape as shown. The elliptical curvature along the first axis, y, of the free-form element 16 provides the first and second foci of the element with which the first and second scanners 14, 18 coincide respectively. This shape and positioning of the free-form element 16 provides aberration correction whilst maintaining an apparent point source of incident light at the pupillary point of the eye 22 and an apparent point source of return light at the first scanner 14.

In this embodiment. the free-form element 16 is positioned in the ophthalmoscope 10 such that the first, y, axis of the element forms a substantially vertical axis and the second, x, axis of the element forms a substantially horizontal axis. It will be appreciated, however, that the free-form element may be positioned in the ophthalmoscope such that the first axis of the element forms a substantially horizontal axis and the second axis of the element forms a substantially vertical axis.

The shape of the free-form element 16 is defined to produce aberration correction of each of the beams of return light at the apparent point source at the first scanner 14 originating from different locations of the fundus. This produces beams of return light which, at the apparent point source at the first scanner 14, have a substantially uniform divergence in a direction of the beams substantially orthogonal to a direction of travel of the beams and substantially parallel to the second axis of the free-form element 16 i.e., in this embodiment, a horizontal dimension of the return beams. The free-form element 16 corrects aberration in a horizontal dimension of each of the beams of return light. The aberration correction of the free-form element 16 does not result in aberration correction in a vertical dimension of the beams of return light. Each of the beams of return light has a different converging/diverging vertical dimension.

The shape of the free-form element 16 also provides aberration correction of each of the beams of incident light incident on different locations of the fundus of the eye 22. This produces beams of incident light which, at the apparent point source at the pupilliary point of the eye 22, have a substantially uniform divergence in a direction of the beams substantially orthogonal to a direction of travel of the beams and substantially parallel to the second axis of the free-form element 16 i.e., in this embodiment, a horizontal dimension of the incident beams.

Figure 3:
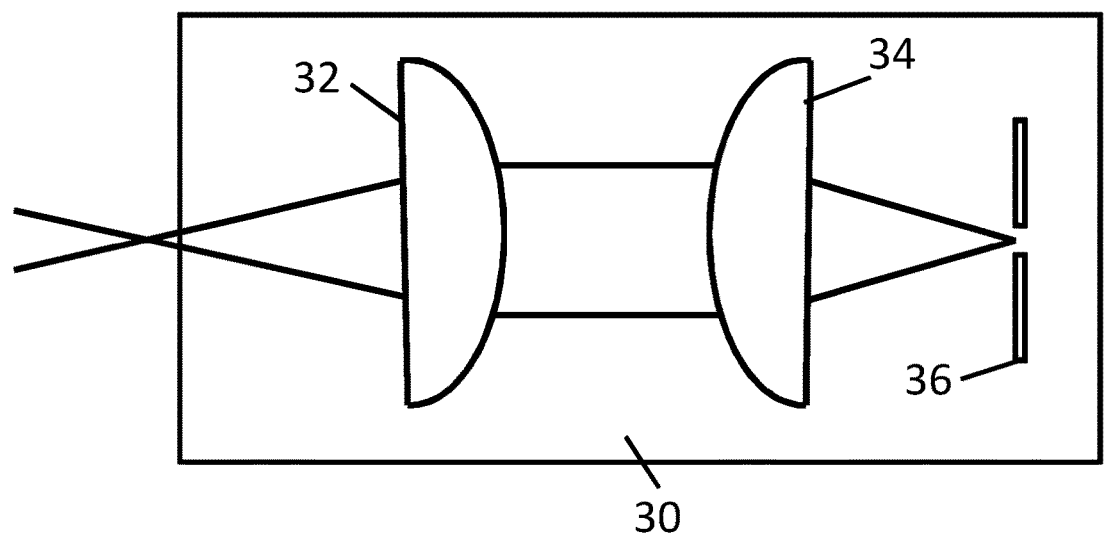
FIG. 3 is a schematic representation of a top view of a fundus return light separation apparatus of the ophthalmoscope of FIG. 1.

Referring to FIGS. 1 and 3, the ophthalmoscope 10 comprises return light detection apparatus 30 positioned in the ophthalmoscope 10 to receive the beams of return light from the fundus of the eye 22 via the first scanner 14 and the beam splitter 24. The return light detection apparatus 30 comprises a collimating lens 32, a focussing lens 34, which is an aspherical or spherical lens, and a slit aperture 36. The slit aperture 36 comprises a first, long, dimension of approximately 2 mm and a second, short, dimension of approximately 250 μm.

The collimating lens 32 is used to focus the plurality of beams of return light originating from different locations of the fundus to produce beams of return light which are collimated in the direction of the light substantially orthogonal to a direction of travel of the light and substantially parallel to the second axis of the free-form element 16 i.e., in this embodiment, a horizontal dimension of the return beams. As the shaping of the free-form element 16 produces substantially uniform divergence of the beams of return light from any location of the fundus, the same lens 32 can be used to produce collimation of each of beams of return light from each location of the fundus.

The focussing lens 34 and the slit aperture 36 are positioned after the collimating lens 32 with respect to the path of each beam of return light, as shown. The slit aperture 36 is positioned in a plane confocal with the fundus of the eye 22. The focussing lens 34 is positioned before the slit aperture 36 such that it focusses each beam of return light at the fundus confocal plane. In the horizontal, or width, dimension of each beam of return light, parallel to the second, x, axis of the first scan transfer element 16, the beam is collimated. In the vertical, or height, dimension of the beam of return light, the beam is either converging or diverging. The focussing lens 34 focusses each beam of return light from the fundus to form a line of return light extending above and below the optical axis of the lens 34. The first, long, axis of the slit aperture 36 is positioned substantially parallel with each line of return light, and the line of light produced by each beam of return light substantially passes through the slit aperture 36 and is detected.

Return light from other structures, such as the cornea of the eye 22 and elements of the ophthalmoscope 10, will not be focussed by the focussing lens 34 into a line of light and will substantially not pass through the slit aperture 36 i.e. are substantially filtered out. This leads to an improvement in confocal detection of the fundus return light.

Figure 4:
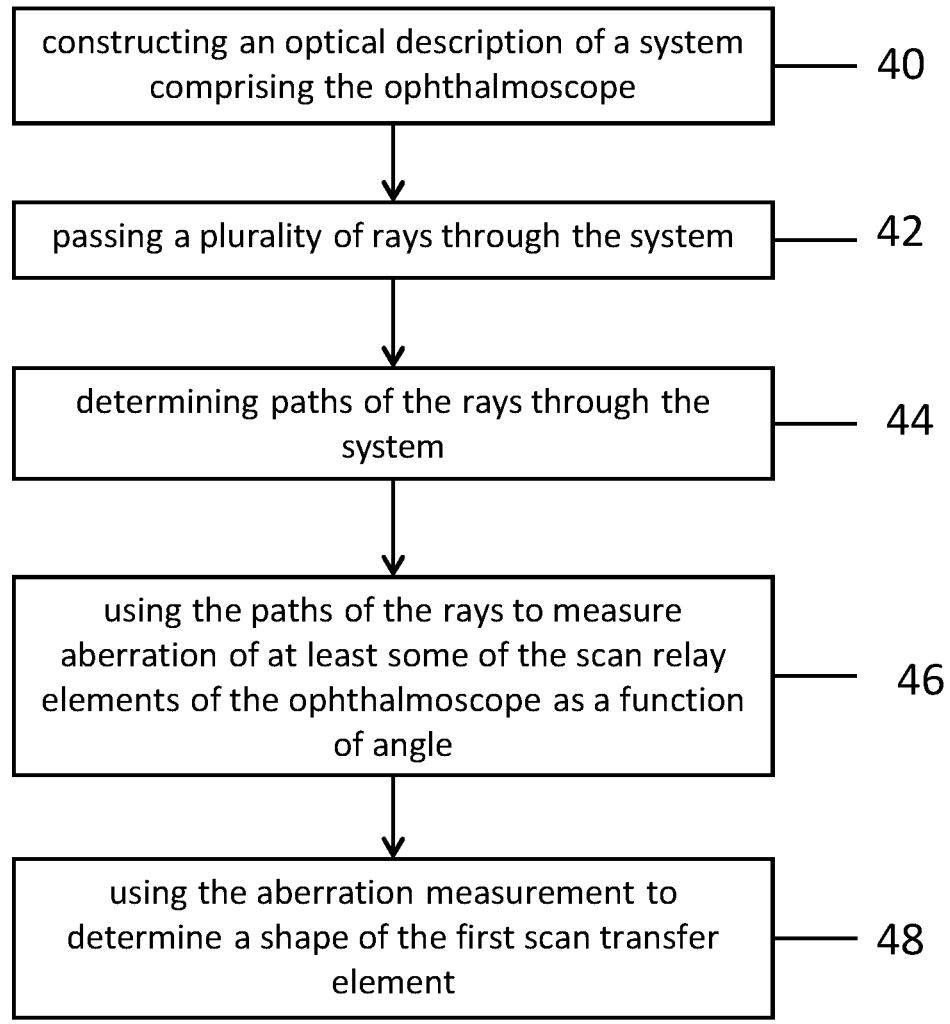
FIG. 4 is a flow chart of a method of defining a shape of the first scan transfer element of FIG. 2 used in the ophthalmoscope of FIG. 1.

Referring to FIG. 4, a method of defining a shape of the free-form first scan transfer element 16 of FIG. 2 used in the ophthalmoscope 10 of FIG. 1 is illustrated. This comprises constructing an optical description of a system comprising the ophthalmoscope (40), passing a plurality of rays through the system (42), determining paths of the rays through the system (44), using the paths of the rays to measure aberration of at least some of the elements of the ophthalmoscope as a function of angle (46) and using the aberration measurement to determine a shape of the free-form element (48). The method may further provide compensation for aberrations of a model eye, by constructing an optical description of a system comprising the ophthalmoscope and the model eye, passing a plurality of rays through the system to impinge at a plurality of angles on a surface of the model eye, determining paths of the rays through the system, using the paths of the rays to measure aberration of at least some of the elements of the ophthalmoscope and the model eye as a function of angle, and using the aberration measurement to determine a shape of the free-form element.

The invention claimed is:
1. An ophthalmoscope comprising:
a light source, a first scanner, a first scan transfer element, a second scanner, and a second scan transfer element, which provide a two-dimensional scan of incident light from an apparent point source at a pupillary point of the eye onto the fundus of the eye, and which descan a two-dimensional scan of return light from the fundus of the eye to provide return light from an apparent point source at the first scanner,
wherein the first scan transfer element comprises a free-form element which has a shape comprising curvature in each of first and second substantially orthogonal axes of the free-form element and defined to provide aberration correction of the return light to produce return light from any location of the fundus of the eye, which, at the apparent point source at the first scanner, has a substantially uniform divergence in a direction of the light which is substantially orthogonal to a direction of travel of the light and substantially parallel to the second axis of the free-form element.

2. An ophthalmoscope according to claim 1 in which the free-form element comprises a reflective element.

3. An ophthalmoscope according to claim 1 in which the free-form element comprises a static element.

4. An ophthalmoscope according to claim 1 in which the curvature along the first axis is defined by an ellipse.

5. An ophthalmoscope according to claim 1 in which the curvature along the second axis is defined by a pre-determined mathematical function.

6. An ophthalmoscope according to claim 5 in which the pre-determined mathematical function comprises at least one polynomial function.

7. An ophthalmoscope according to claim 1 in which the free-form element is substantially rectangular in shape and the first axis of the free-form element is at an angle to a long axis of the rectangular shape and the second axis of the free-form element is at an angle to a short axis of the rectangular shape.

8. An ophthalmoscope according to claim 1 further comprising a lens positioned after the first scanner, which is used to focus the return light to produce return light from any location of the fundus which is collimated in the direction of the light substantially orthogonal to the direction of travel of the light and substantially parallel to the second axis of the free-form element.

9. An ophthalmoscope according to claim 1 in which the two-dimensional scan of return light from the fundus of the eye comprises a plurality of beams of return light, each beam of return light originating from a different location of the fundus of the eye.

10. An ophthalmoscope according to claim 9 in which the free-form element has a shape defined to provide aberration correction of each beam of return light to produce beams of return light which, at the apparent point source at the first scanner, have a substantially uniform divergence in a direction of the beams substantially orthogonal to a direction of travel of the beams and substantially parallel to the second axis of the free-form element.

11. An ophthalmoscope according to claim 10 further comprising a lens positioned after the first scanner, which is used to focus the plurality of beams of return light originating from different locations of the fundus to produce beams of return light which are collimated in the direction of the light substantially orthogonal to the direction of travel of the light and substantially parallel to the second axis of the free-form element.

12. An ophthalmoscope according to claim 1 in which the free-form element has a shape defined to provide aberration correction of the incident light on the fundus of the eye.

13. An ophthalmoscope according to claim 1 further comprising fundus return light separation apparatus comprising at least one lens and an aperture.

14. An ophthalmoscope according to claim 13 in which the lens is an aspherical lens.

15. An ophthalmoscope according to claim 13 in which the aperture is a slit aperture.

16. An ophthalmoscope according to claim 15 in which the lens is positioned in the ophthalmoscope to receive return light from the fundus of the eye via the first scanner and focusses the fundus return light into a line of return light at a plane confocal with the fundus of the eye.

17. An ophthalmoscope according to claim 16 in which the slit aperture is positioned in the ophthalmoscope after the lens in an optical path of the return light at the plane confocal with the fundus of the eye such that a long axis thereof is substantially parallel with the line of return light and the line of return light substantially passes through the slit aperture.

18. A first scan transfer element for use in the ophthalmoscope of claim 1.

19. A method of defining a shape of a first scan transfer element for use in the ophthalmoscope of claim 1, comprising
   (i) constructing an optical description of a system comprising the ophthalmoscope,
   (ii) passing a plurality of rays through the system,
   (iii) determining paths of the rays through the system,
   (iv) using the paths of the rays to measure aberration of at least some of the elements of the ophthalmoscope as a function of angle, and
   (v) using the aberration measurement to determine a shape of the first scan transfer element.

* * * * *